United States Patent
Kim et al.

(10) Patent No.: US 11,484,716 B2
(45) Date of Patent: Nov. 1, 2022

(54) ARTIFICIAL RETINA STIMULATOR AND APPARATUS WITH IMAGE JITTERING FUNCTION

(71) Applicants: KOREA UNIVERSITY RESEARCH AND BUSINESS FOUNDATION, Seoul (KR); Gachón University of industry-Academic Cooperation Foundation, Gyeonggi-do (KR)

(72) Inventors: Seong Woo Kim, Seoul (KR); Jung Suk Kim, Gyeonggi-do (KR)

(73) Assignees: KOREA UNIVERSITY RESEARCH AND BUSINESS FOUNDATION, Seoul (KR); GACHON UNIVERSITY OF INDUSTRY-ACADEMIC COOPERATION FOUNDATION, Seoul (KR)

( * ) Notice: Subject to any disclaimer, the term of this patent is extended or adjusted under 35 U.S.C. 154(b) by 126 days.

(21) Appl. No.: 17/040,272

(22) PCT Filed: Oct. 5, 2018

(86) PCT No.: PCT/KR2018/011763
§ 371 (c)(1),
(2) Date: Sep. 22, 2020

(87) PCT Pub. No.: WO2019/190012
PCT Pub. Date: Oct. 3, 2019

(65) Prior Publication Data
US 2021/0008374 A1 Jan. 14, 2021

(30) Foreign Application Priority Data
Mar. 26, 2018 (KR) .................. 10-2018-0034606

(51) Int. Cl.
*A61N 1/36* (2006.01)
*A61N 1/05* (2006.01)

(52) U.S. Cl.
CPC ....... *A61N 1/36167* (2013.01); *A61N 1/0543* (2013.01); *A61N 1/36046* (2013.01); *A61N 1/36185* (2013.01)

(58) Field of Classification Search
CPC .............. A61N 1/36167; A61N 1/0543; A61N 1/36046; A61N 1/36185; A61N 1/36128; A61F 2/14
See application file for complete search history.

(56) References Cited

U.S. PATENT DOCUMENTS

2002/0010496 A1* 1/2002 Greenberg ......... A61N 1/36046
607/54
2007/0255319 A1* 11/2007 Greenberg ........... A61N 1/0543
607/2

(Continued)

FOREIGN PATENT DOCUMENTS

JP 2002325851 A 11/2002
JP 2009535075 A 10/2009

(Continued)

*Primary Examiner* — Eugene T Wu
(74) *Attorney, Agent, or Firm* — Tarolli, Sundheim, Covell & Tummino LLP (57) ABSTRACT

Disclosed is an artificial retinal stimulator and an artificial retinal device which are for providing image jittering. The artificial retinal stimulator for providing the image jittering includes: a photodiode configured to sense light stimulation and generate a current based on an intensity of the stimulation; a pulse generator configured to generate a pulse to be provided to a corresponding stimulation electrode on the basis of the current coming from the photodiode; a switch configured to connect an output terminal of the pulse generator and ground; and a jittering switch configured to determine whether to transfer the generated pulse to the (Continued)

corresponding stimulation electrode or to transfer to a stimulation electrode corresponding to another artificial retinal stimulator. According to the present disclosure, an image jittering function capable of emulating an eye blinking effect is provided, so that it is possible to enable a low vision patient to see images better.

9 Claims, 6 Drawing Sheets

(56) References Cited

U.S. PATENT DOCUMENTS

| | | | |
|---|---|---|---|
| 2014/0236260 A1* | 8/2014 | McDermott | A61N 1/36046 607/54 |
| 2016/0082250 A1 | 3/2016 | Matteucci et al. | |

FOREIGN PATENT DOCUMENTS

| | | |
|---|---|---|
| KR | 20060018901 A | 3/2006 |
| KR | 20180025468 A | 3/2018 |

* cited by examiner

FIG. 7

ARTIFICIAL RETINA STIMULATOR AND APPARATUS WITH IMAGE JITTERING FUNCTION

RELATED APPLICATIONS

The present invention is a U.S. National Stage under 35 USC 371 patent application, claiming priority to Serial No. PCT/KR2018/011763, filed on 5 Oct. 2018; which claims priority of 10-2018-0034606, filed on 26 Mar. 2018, the entirety of both of which are incorporated herein by reference.

FIELD

The present disclosure relates to an artificial retinal stimulator and an artificial retinal device, and more particularly to a sub-type artificial retinal based artificial retinal stimulator which includes an image jittering function in order to improve the visual function of a low vision patient.

BACKGROUND

There are three basic methods for improving the visual function of a low vision patient.

The three methods include reducing a distance between eye and object (distance reduction), enlarging the size of the object (size enlargement), and positioning an image large close to eye by using a magnifying telescope, etc. (angle enlargement). However, these enlargements often narrow a field of view, change the sense of depth, and break the harmony between the visible sense of vision and movement, making it difficult to perform an appropriate body functional cooperation. Therefore, other methods other than the enlargement must be considered to improve the vision of the low vision patients. In general, a reading speed increases when the size of a letter increases. However, when the size of a letter increases beyond a certain critical print size, the increase in the size of a letter does not help to improve the visual function anymore. An increase in contrast sensitivity is also known to play an important role in improving the visual function such as reading speed, etc. However, it is also known that the increase in contrast sensitivity cannot plays such a role any longer when the size of a letter reaches the critical print size, that is to say, when the size of a letter increases to some extent or more. Therefore, it can be seen that the increase in the size of a letter or the increase in contrast sensitivity cannot be greatly helpful anymore to ultra-low vision patients (less than 0.01) who use an artificial retinal stimulator. In other words, methods other than the contrast sensitivity should be considered for these patients.

SUMMARY

The purpose of the present disclosure is to provide an artificial retinal stimulator including an image jittering function in order to improve the visual function of a low vision patient.

One embodiment is an artificial retinal stimulator providing image jittering. The artificial retinal stimulator may include a photodiode which senses light stimulation and generates a current based on an intensity of the stimulation; a pulse generator which generates a pulse to be provided to a corresponding stimulation electrode on the basis of the current coming from the photodiode; a switch which connects an output terminal of the pulse generator and ground; and a jittering switch which determines whether to transfer the generated pulse to the corresponding stimulation electrode or to transfer to a stimulation electrode corresponding to another artificial retinal stimulator.

The jittering switch may be provided between the photodiode and the pulse generator or may be provided to the output terminal of the pulse generator.

The jittering switch may include a first switch which transfers the generated pulse to the corresponding stimulation electrode when connecting, and a second switch which transfers the generated pulse to the stimulation electrode corresponding to another artificial retinal stimulator when connecting.

The pulse generated by the pulse generator may be a biphasic pulse.

Another embodiment is an artificial retinal device for providing image jittering may include a plurality of the artificial retinal stimulators and a stimulation electrode corresponding to each of the plurality of artificial retinal stimulators.

A jittering switch of each of the plurality of artificial retinal stimulators may include a first switch and a second switch. The first switch may perform a connection to the corresponding stimulation electrode. The second switch may perform a connection to a stimulation electrode corresponding to adjacent artificial retinal stimulators among the plurality of artificial retinal stimulators.

The artificial retinal device for providing the image jittering may further include a controller which controls on/off of the first and second switches included in the jittering switch of each of the plurality of artificial retinal stimulators. The controller may control to switch off the second switch when the first switch is switched on, and to switch on the second switch when the first switch is switched off. In addition to this, the controller may alternately switch on the first switch and the second switch in a regular time period.

The controller may simultaneously switch on or off all of the first switches and all of the second switches included in the plurality of artificial retinal stimulators.

The embodiment of the present disclosure provides an image jittering effect by changing an electrode which is stimulated for the same stimulation.

The embodiment of the present disclosure provides an image jittering function capable of emulating an eye blinking effect, thereby enabling a low vision patient to see images better.

DETAILED DESCRIPTION

Parts irrelevant to the description will be omitted for a clear description of the present disclosure. The same or similar reference numerals will be assigned to the same or similar components throughout this patent document.

Throughout the specification, when it is mentioned that a portion is "connected" to another portion, it includes not only "is directly connected" but also "electrically connected" with another element placed therebetween. Meanwhile, in the case where a component is referred to as being "directly connected" to other components, it should be understood that there is no component therebetween. Additionally, when it is mentioned that a portion "includes" an element, it means that the portion does not exclude but further includes other elements unless there is a special opposite mention.

When it is mentioned that a part is placed "on" another part, this means that a part may be placed directly on another part or a third part may be accompanied between them. In contrast, when it is mentioned that a part is placed "directly on" another part, this means that a third part may not be accompanied between them.

While terms such as first, second, third, etc., are used to describe various parts, components, regions, layers, and/or sections, these terms are not limited thereto. These terms are only used to distinguish one part, component, region, layer or section from another part, component, region, layer or section. Thus, a first part, component, region, layer or section to be described below can be referred to as a second part, component, region, layer or section without departing from the scope of the present disclosure.

The terminologies used herein are provided for description of only specific embodiments of the present disclosure and are not intended to limit the present disclosure. Singular forms used herein include plural form thereof unless phrases have the meanings opposite thereto clearly. The meaning of "including" used in this specification embodies specific characteristics, regions, integers, steps, operations, elements, and/or components, and does not exclude the existence or addition of other specific characteristics, regions, integers, steps, operations, elements, and/or components.

Spatially relative terms, such as "under", "over" and the like, may be used to more easily describe a relationship of one portion to another portion shown in the drawing. These terms are intended to include not only meanings intended in the drawing but other meanings or operations of a device in use. For example, if the device is turned upside down in the drawing, a portion described as being "under" other portions is described as being "over" other portions. Thus, the exemplary term "under" includes both an up direction and a down direction. The device may rotate by 90 degrees or at other angles, and the spatially relative terms are construed accordingly.

Unless otherwise defined, all terms used herein including technical and scientific terms have the same meaning as commonly understood by one of ordinary skill in the art to which the present invention belongs. Commonly used terms defined in the dictionary are additionally construed as having meanings conforming to related technology documents and currently disclosed contents. As long as terms are not clearly defined, the terms should not be ideally or excessively construed as formal meaning.

Hereafter, an embodiment of the present invention will be described in detail with reference to the accompanying drawings such that those skilled in the art can easily carry out the embodiment. However, the present invention may be embodied in various forms and is not limited to the embodiment described in the present specification.

Research has shown that people with normal vision see low spatial frequency images better when they blink at 5 to 10 Hz for image contrast. Also, considering that low vision patients need large letters or images in order to improve visual perception, a method for increasing the visual sensitivity by modulating the contrast of the target object may be very helpful to low vision patients who recognize an image that is mainly composed of low spatial frequencies. Similar research has shown that contrast sensitivity is increased when stimulation of full-field flicker is given to patients with visual impairments.

Even when a person with normal vision watches a stationary object, the eyes move continuously, causing jittering of the image of the object on the retina. There are three types of these involuntary movements.

1) Tremor: a periodic motion with about 90 Hz and amplitude of about 1 arcmin.

2) Drift: a slow eye movement with an amplitude which may be up to 1 arcmin.

3) Microsaccades (fine eye movement): an irregular rapid eye movement which may cause shaking with 0.25 to 5 Hz and amplitude of 4 to 30 arccmin.

The purpose of these eye movements may be a reaction to neuroadaptation. In other words, the purpose of these eye movements may be considered to act to temporarily burst a neural spike by shaking a static image formed on the receptive fields of the retinal optic nerve. This can help the parvocellular visual pathways, which have a small receptive field responsible for cognition of delicate parts, to maintain continuously their activities. In normal people, in order to maintain cognition by continuously watching a still image with a high spatial frequency while the stimulus continues, the amplitude of physiological microsaccades is provided as a sufficient amplitude. On the other hand, nerves which mainly react to stimuli of low spatial frequency and high temporal frequency and are present in nerve cells around the retina (magnocellular pathways) responsible for a larger receptive field react only at a very short moment when the stimulation occurs and disappears. Therefore, the movement of the retinal image caused by the microsaccades is not sufficient to cause a nerve reaction while watching a still low spatial frequency image. Accordingly, in order to increase the sensitivity to a low spatial frequency image, stimulation with a greater amplitude is required. Considering that, in patients with impaired central vision, the visual stimulation in the low spatial frequency region processed by the nerve cells around the retina which have such a large receptive field plays a main role in visual information processing, jittering the image formed on the retina at a certain frequency and to a certain size is helpful to the low vision patients.

Large-amplitude eye movements in people with normal vision cause degradation rather than increase in image information recognition, whereas much research has shown that jittering of an image with an appropriate frequency and amplitude in patients with reduced vision due to age-related macular degeneration, etc., rather improves a reading speed and object recognition function. In particular, it can be seen that when patients with severe low vision less than 0.1 are stimulated by jittering the image, the visual function is more improved than that of the static image stimulation. Also, it has been reported that when image jittering at 1 to 5 Hz and at an amplitude of 0.5 degrees or 1 degree results in the best reading speed or the best recognition function of a facial expression. Meanwhile, it has been reported that the vision function is rather deteriorated above 10 Hz or more.

Based on these research results, the present disclosure provides an artificial retinal stimulator capable of providing the jittering function to help improve recognition capability of patients with low vision.

An artificial retinal device may be largely divided into two types according to the method for delivering visual stimulation to the artificial retinal stimulator. One is a camera type that stimulates a designated electrode by obtaining image information with a camera and by processing the information, and the other is a photodiode type that recognizes light by a photodiode and stimulates an electrode located next to it not just above (not on the same coordinates).

In the photodiode type artificial retinal stimulator, since the photodiode has to accept a light signal, an opaque electrode cannot be placed on the photodiode but has to be placed next to it. Strictly speaking, this inevitably leads to inconsistency between an area where light stimulates the retina and an area where the retina is stimulated. However, considering that the patients receiving the artificial retinal stimulator are ultra-low vision patients with low vision of 0.01 or less, the position mismatch of several tens of um to 100 um between the photodiode and the electrode may not cause practical discomfort to patients in life, in terms of using information of very low spatial frequency. The positional mismatch between the light receptor and the stimulator, which is inherently unavoidable due to such a design principle of the photodiode, can be used by being combined with the image jittering, which is one of vision improvement techniques for low vision patients.

The camera type stimulator can stimulate the electrode by applying the image jittering during the image processing. However, the photodiode has to implement the image jittering in a circuit. In the present disclosure, in order to implement the image jittering in the artificial retinal stimulator using the photodiode, two adjacent connected stimulation electrodes and the photodiode located between therebetween are alternately connected by using a switch, so that the image jittering is implemented by alternately transmitting an electrical signal generated by the light stimulation entering the photodiode to the two electrodes.

In general, a sub-type artificial retinal device is composed of a plurality of pixels, and may be implemented in the form of a two-dimensional array. That is, the sub-type artificial retinal device may be implemented by dividing the retina in a two-dimensional manner and by placing the pixels at each divided point.

Also, each pixel may include the artificial retinal stimulator and the stimulation electrode.

Figure 1:
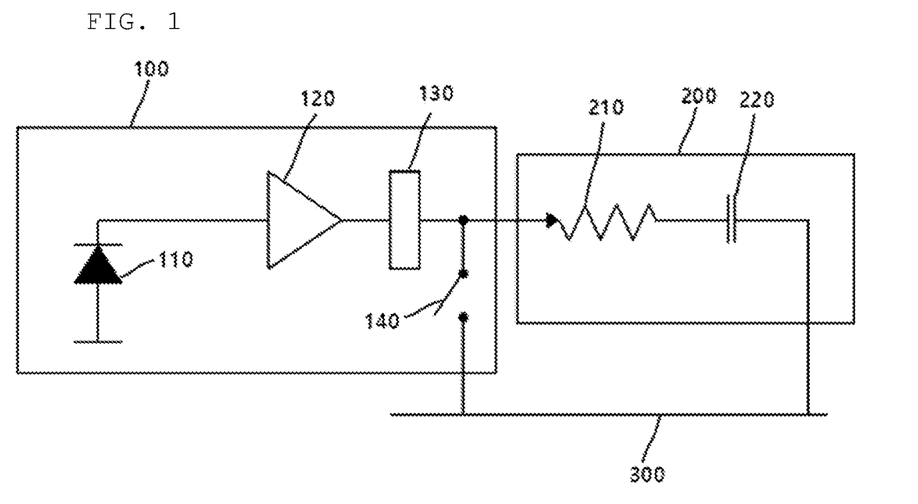
FIG. 1 shows a structure of one pixel of a general sub-type artificial retinal device.

FIG. 1 shows a structure of one pixel of a general sub-type artificial retinal device.

Referring to FIG. 1, one pixel of the general sub-type artificial retinal device may include an artificial retinal stimulator 100 and a stimulation electrode 200.

The stimulation electrode 200 performs a function of transmitting stimulation from the artificial retinal stimulator 100 to a retinal tissue, and is generally modeled by a resistor 210 and a capacitor 220 connected to ground 300.

The artificial retinal stimulator 100 is composed of a photodiode 110 and a pulse generator. The photodiode 110 senses the intensity of light. The pulse generator amplifies a dark current generated by the photodiode 110, converts the amplified dark current into a pulse to be provided to the stimulation electrode 200 and outputs it. Here, the pulse generator may be composed of a converter 120 and a driver 130, and in particular, the pulse may be a biphasic pulse. Also, a switch 140 may be further provided on the output terminal of the driver 130 of the pulse generator. The switch 140 connects the output terminal of the driver 130 to the ground 300 in order to achieve a charge balance after transmitting a stimulation pulse.

Figure 2:
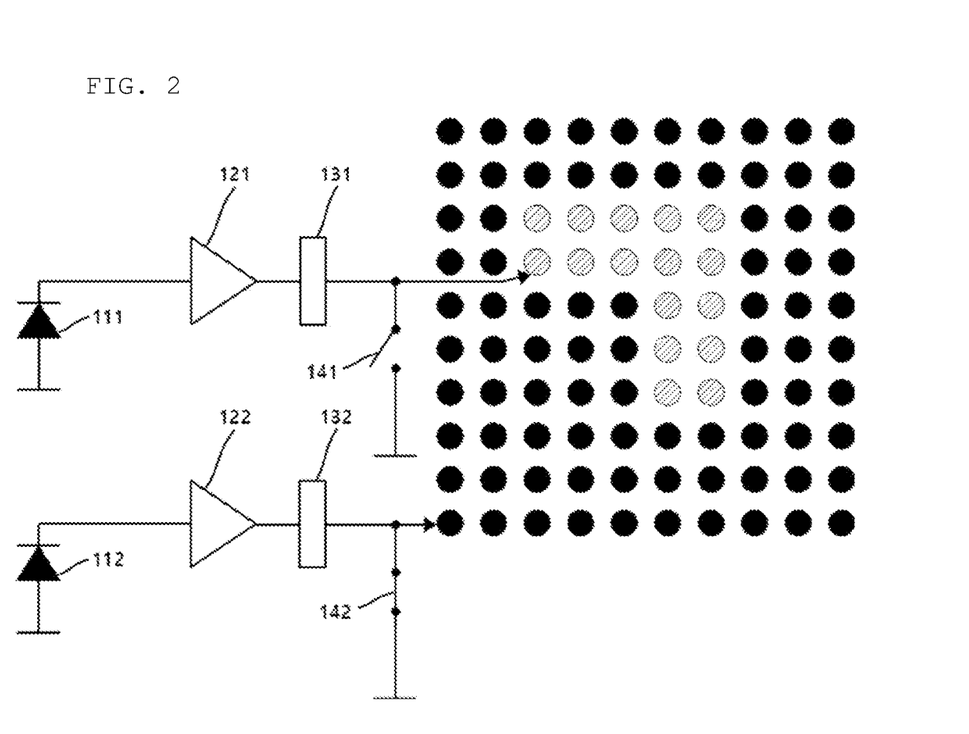
FIG. 2 shows an example of stimulation in the artificial retinal device composed of a plurality of pixels.

FIG. 2 shows an example of stimulation in the artificial retinal device composed of a plurality of pixels.

In FIG. 2, as an example, only artificial retinal stimulators for two pixels are shown. However, in practice, the artificial retinal stimulators exist for all pixels.

As shown in FIG. 2, when oblique-lined portions are stimulated, the photodiode 111 of a pixel which receives light stimulation of the oblique-lined portions receives the light stimulation and outputs a current. The converter 121 and the driver 131 receive the current and output a biphasic pulse. Meanwhile, the photodiode 112 cannot output the current in portions which are not stimulated, and the switch 142 remains connected such that the output terminal of the driver 132 is connected to the ground 300. When the stimulation of the "oblique-lined portions" continues to the artificial retina, a conventional artificial retinal device continues the stimulation shown in FIG. 2 without image jittering.

Figure 3:
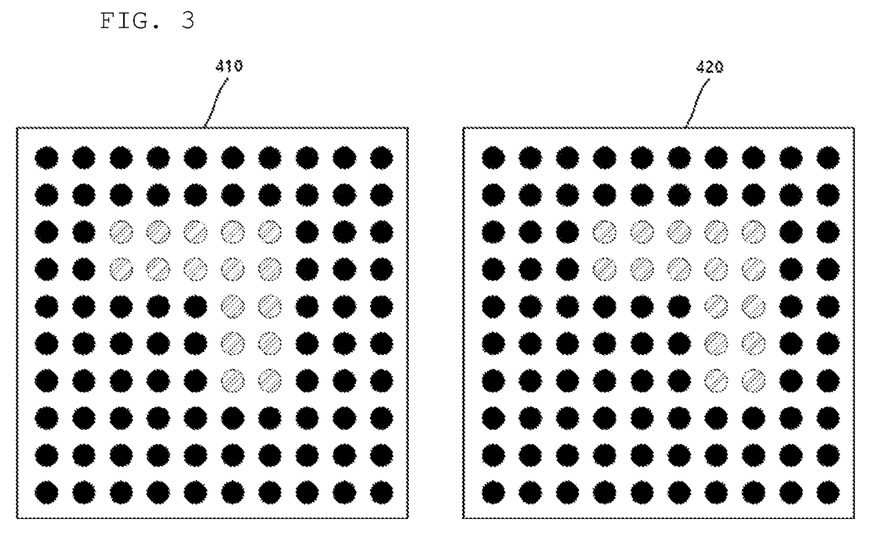
FIGS. 3 and 4 show embodiments in which a stimulation range is changed for image jittering proposed in the present invention.
Figure 4:
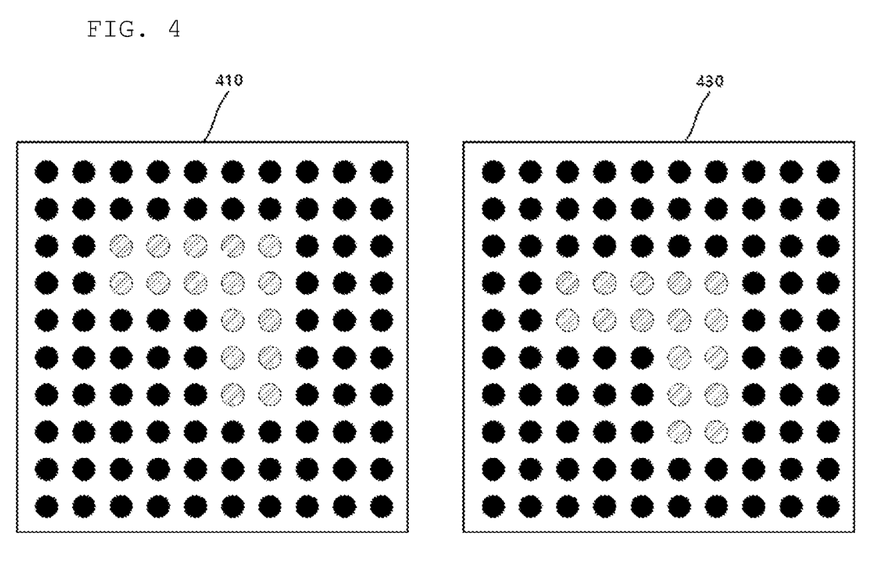

FIGS. 3 and 4 show embodiments in which a stimulation range is changed for the image jittering proposed in the present invention.

Referring to FIGS. 3 and 4, during a period of time when a constant stimulation of the "oblique-lined portions" continues, the first stimulation 410 of the "oblique-lined portions" is delivered to the stimulation electrode of the artificial retinal device, and then, in a certain period of time, the stimulation 420 which has moved to the right by one pixel or the stimulation 430 which has moved downward by one pixel is delivered to the stimulation electrode of the artificial retinal device.

Figure 5:
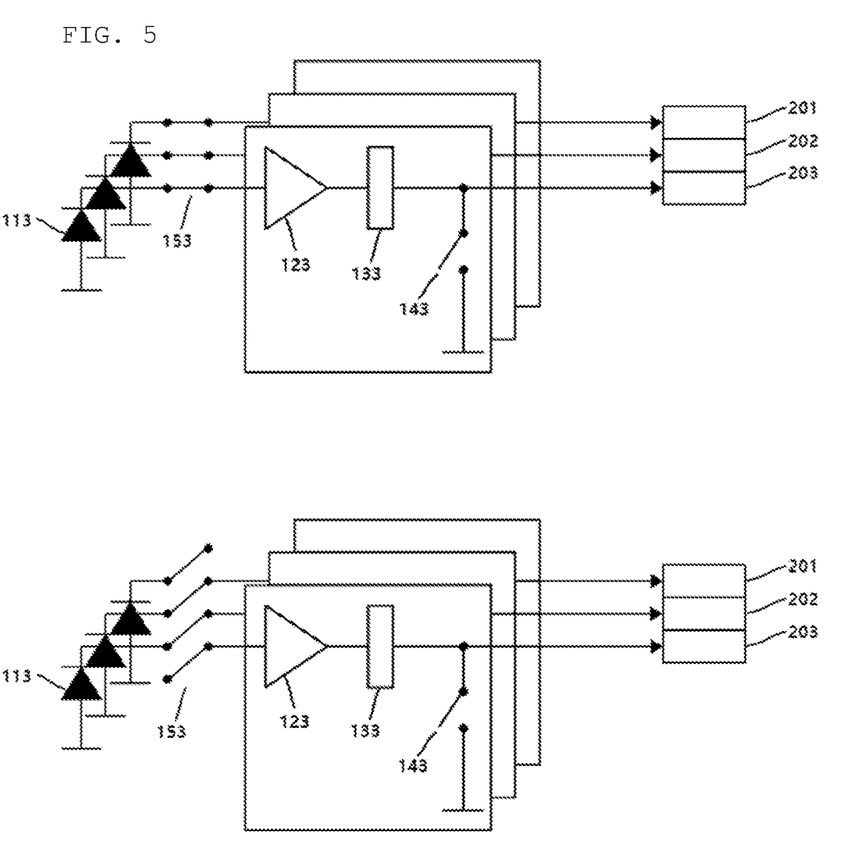
FIG. 5 shows an artificial retinal stimulator equipped with an image jittering function in accordance with the embodiment of the present disclosure.

FIG. 5 shows the artificial retinal stimulator equipped with an image jittering function in accordance with the embodiment of the present disclosure.

Referring to FIG. 5, the artificial retinal stimulator according to the embodiment of the present disclosure further includes a switch 153 between a photodiode 113 and a converter 123 in order to provide the image jittering function. The switch 153 transfers the current flowing out from the stimulated photodiode 113 to its own converter 123 and driver 133 for a certain period of time, and then is switched to transmit the current to the converter and the driver of an adjacent artificial retinal stimulator. Here, the adjacent artificial retinal stimulator may be located above or below by one pixel or on the left or on the right in a pixel array of the artificial retinal device.

Also, the switch 153 may transmit the current coming from the photodiode 113 while periodically switching to the converter of the adjacent artificial retinal stimulator and its own converter. That is, even if the same stimulation continues to the photodiode 113, the stimulation electrode to be stimulated is changed between a stimulation electrode 203 corresponding to itself and a stimulation electrode 202 corresponding to the adjacent artificial retinal stimulator. As a result, the image jittering can occur, when viewing the entire artificial retinal device.

Figure 6:
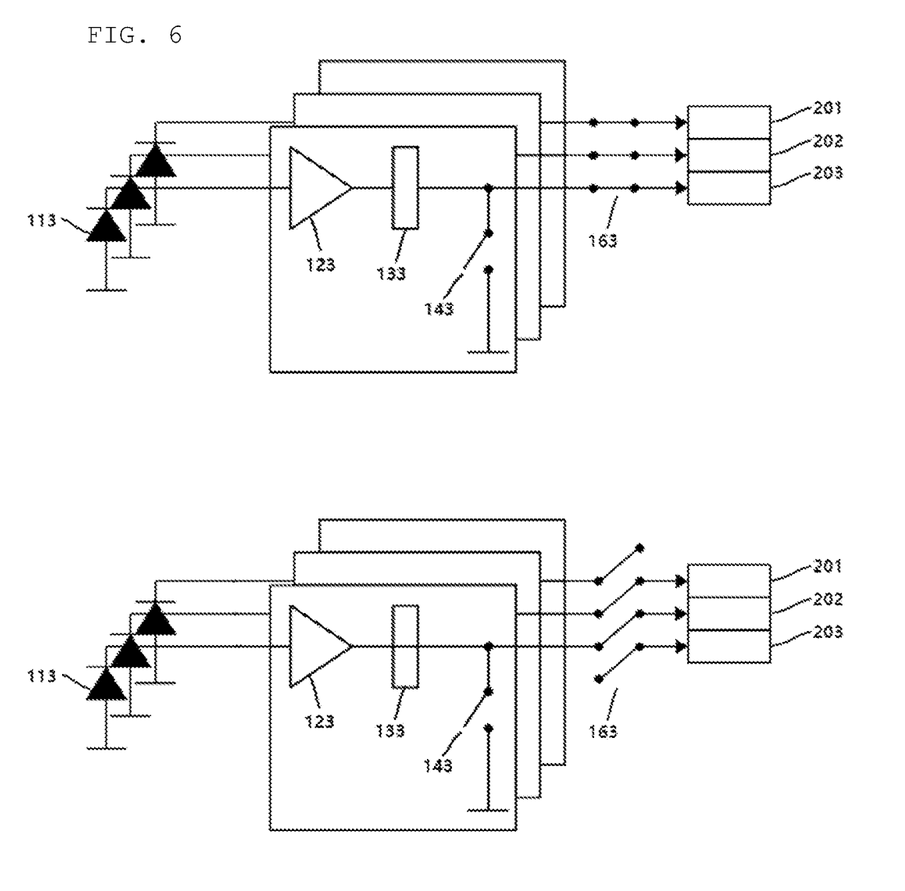
FIG. 6 shows an artificial retinal stimulator equipped with the image jittering function in accordance with another embodiment of the present disclosure.

FIG. 6 shows an artificial retinal stimulator equipped with the image jittering function in accordance with another embodiment of the present disclosure.

Referring to FIG. 6, the artificial retinal stimulator according to another embodiment of the present disclosure further includes a switch 163 on the output terminal of the driver 133 in order to provide the image jittering function. That is, the switch 163 is provided before the stimulation electrodes 201 to 203 that the biphasic pulse output from the driver 133 enters, and the output terminal of the driver 133 is connected to the stimulation electrode 203 corresponding to itself for a certain period of time. Then, the output terminal is connected to the stimulation electrode 202 corresponding to the adjacent artificial retinal stimulator. Here, the adjacent artificial retinal stimulator may be located above or below by one pixel or on the left or on the right in a pixel array of the artificial retinal device.

Also, the switch 163 is periodically switched to transmit the biphasic pulse output from the output terminal of the driver 133 to the stimulation electrode 203 corresponding to itself or the stimulation electrode 202 corresponding to the adjacent artificial retinal stimulator. That is, even if the same stimulation continues to the photodiode 113, the stimulation electrode to be stimulated is changed between a stimulation electrode 203 corresponding to itself and a stimulation electrode 202 corresponding to the adjacent artificial retinal stimulator. As a result, the image jittering can occur, when viewing the entire artificial retinal device.

Figure 7:
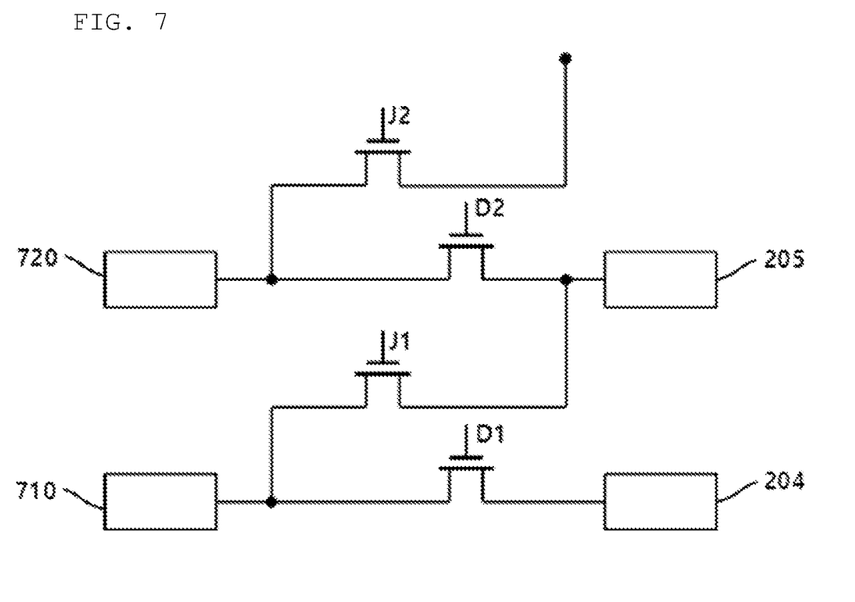
FIG. 7 shows a switch structure added for implementing the image jittering function in accordance with the embodiment of the present disclosure.

FIG. 7 shows a switch structure added for implementing the image jittering function in accordance with the embodiment of the present disclosure.

Referring to FIG. 7, a switch added in order to implement the image jittering function according to the embodiment of the present disclosure may be composed of two semiconductor switches D1 and J1 enabling the output terminal of the artificial retinal stimulator 710 of the $N^{th}$ pixel to be connected to a stimulation electrode 204 of the $N^{th}$ pixel and a stimulation electrode 205 of the $(N+1)^{th}$. Here, the semiconductor switch may be a transistor, a field effect transistor (FET), SCR, TRIAC, or the like.

When the semiconductor switch D1 is turned on by applying a high voltage to the semiconductor switch D1 and the semiconductor switch J1 is turned off by applying a low voltage to the semiconductor switch J1, the biphasic pulse output from the artificial retinal stimulator 710 of the $N^{th}$ pixel may be applied to the $N^{th}$ stimulation electrode 204. Then, when the semiconductor switch J1 is turned on by applying a high voltage to the semiconductor switch J1 and the semiconductor switch D1 is turned off by applying a low voltage to the semiconductor switch D1, the biphasic pulse output from the artificial retinal stimulator 710 of the $N^{th}$ pixel may be applied to the $(N+1)^{th}$ stimulation electrode 205.

Similarly, the biphasic current output from an artificial retinal stimulator 720 of the $(N+1)^{th}$ pixel by two semiconductor switches D2 and J2 may be applied to the stimulation electrode 205 of the $(N+1)^{th}$ pixel or the stimulation electrode of the $(N+2)^{th}$ pixel.

A separate controller (not shown) may be included in order to control the on/off of the switch. Here, the controller (not shown) may control such that the two semiconductor switches D1 and J1 or D2 and J2 are periodically turned on/off. Here, the controller may control the periodic on/off time according to a preset value. Also, the controller (not shown) may control such that n number of the semiconductor switches D1 to Dn are synchronized and switched from on to off or from off to on simultaneously. The controller (not shown) may control such that n number of other semiconductor switches J1 to Jn are synchronized and switched from on to off or from off to on simultaneously.

Here, the controller may adjust the periodic on/off time between 0.2 seconds and 1 second. In other words, a period of 1 to 5 Hz can be obtained. In particular, in order to form the period, the controller may reduce a carrier frequency of 2 MHz to 1 to 5 Hz by using a clock divider. Also, in the frequency of jittering, the period may be changed by the patient with an external regulator so as to reflect each individual difference.

As described above, the artificial retinal stimulator and the artificial retinal device including the same as presented in the present disclosure can implement the image jittering function, thereby further improving the visual function of a low vision patient receiving the artificial retinal device.

Since the embodiments can be embodied in other specific forms without departing from its spirit or essential characteristics, those skilled in the art to which the present disclosure belongs must understand that the foregoing embodiments and advantages are merely exemplary and are not to be construed as limiting the present invention. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. An artificial retinal stimulator for providing image jittering, the artificial retinal stimulator comprising:
   a photodiode configured to sense light stimulation and generate a current based on an intensity of the stimulation;
   a pulse generator configured to generate a pulse to be provided to a corresponding stimulation electrode on the basis of the current coming from the photodiode;
   a switch configured to connect an output terminal of the pulse generator and ground; and
   a jittering switch configured to determine whether to transfer the generated pulse to the corresponding stimulation electrode or to transfer to a stimulation electrode corresponding to another artificial retinal stimulator,
   wherein the jittering switch is provided to an output terminal of the pulse generator.

2. The artificial retinal stimulator of claim 1, wherein the jittering switch comprises:
   a first switch configured to transfer the generated pulse to the corresponding stimulation electrode when connecting; and
   a second switch configured to transfer the generated pulse to the stimulation electrode corresponding to another artificial retinal stimulator when connecting.

3. The artificial retinal stimulator of claim 1, wherein the pulse is a biphasic pulse.

4. An artificial retinal device for providing image jittering, the artificial retinal device comprising:
   a plurality of the artificial retinal stimulators according to claim 1; and
   a stimulation electrode corresponding to each of the plurality of artificial retinal stimulators.

5. The artificial retinal device of claim 4,
   wherein a jittering switch of each of the plurality of artificial retinal stimulators comprises a first switch and a second switch,
   wherein the first switch performs a connection to the corresponding stimulation electrode, and wherein the second switch performs a connection to a stimulation electrode corresponding to adjacent artificial retinal stimulators among the plurality of artificial retinal stimulators.

6. The artificial retinal device of claim 5, further comprising a controller which controls on/off of the first switch and the second switch comprised in the jittering switch of each of the plurality of artificial retinal stimulators.

7. The artificial retinal device of claim 6, wherein the controller switches off the second switch when the first switch is switched on, and switches on the second switch when the first switch is switched off.

8. The artificial retinal device of claim 6, wherein the controller alternately switches on the first switch and the second switch in a regular time period.

9. The artificial retinal device of claim 6, wherein the controller simultaneously switches on or off all of the first switches and all of the second switches comprised in the plurality of artificial retinal stimulators.

\* \* \* \* \*